United States Patent [19]

Smith

[11]  4,046,578
[45]  Sept. 6, 1977

[54] TYPE OF ADHESIVE CEMENT AND CERTAIN IMPROVED PRODUCTS MADE POSSIBLE THEREBY

[76] Inventor: David F. Smith, 101 Briny Ave. No. 607, Pompano Beach, Fla. 33062

[21] Appl. No.: 593,885

[22] Filed: July 7, 1975

[51] Int. Cl.² .............................................. C09K 3/00
[52] U.S. Cl. .................................... 106/35; 106/193 J
[58] Field of Search ..................... 106/35; 260/998.11; 106/193

[56] References Cited

U.S. PATENT DOCUMENTS 3,607,262  9/1971  Ueda ...................................... 96/1.8
3,882,080  5/1975  Schmitt ........................... 260/998.11

OTHER PUBLICATIONS

"The Reaction of Metal Oxides with o-Ethoxybenzoic Acid and Other Chelating Agents" Brauer et al. J. D. Res. June 1958, pp. 547-560.

"Dental Silicate Cements" Wilson, J. Dent. Res., Dec. 1968, pp. 1133-1136.

*Primary Examiner*—Theodore Morris

[57] ABSTRACT

New types of fast setting zinc oxide-polycarboxylic acid adhesive cements are disclosed as well as certain improved products the use of these cements makes possible.

10 Claims, No Drawings

TYPE OF ADHESIVE CEMENT AND CERTAIN IMPROVED PRODUCTS MADE POSSIBLE THEREBY

This application is a continuation-in-part of my co-pending application, Ser. No. 473,751, filed May 28, 1974 now abandoned.

Certain new types of cement have been disclosed by Dennis Clifford Smith (British Pat. No. 1,139,430, Jan. 8, 1969) and by Alan Donald Wilson and Brian Ernest Kent (British Pat. No. 1,316,129, May 9, 1973). These cements were designed for dental use. The former involves the reaction of ZnO with 40-60% aqueous polyacrylic acid of molecular-weight 15000-150000. (I have discovered that polymethacrylic acid is substantially the equivalent of polyacrylic acid in these cements.) The polyacrylic acid solution is relatively expensive. The latter cement involves a high temperature fusion as well as the polyacrylic acid. While these products are undoubtedly excellent for dental use and such use can tolerate their high cost, certain of my uses require a much cheaper product and also a dry, powdery solid acid that is quick to dissolve. It is difficult and expensive to produce such a form of polyacrylic acid. I have discovered very effective adhesive cements that are much cheaper, more readily available in a form convenient to use and controllably settable. My adhesive cement is also more adhesive shortly after wetting and avoids the possibility of skin reaction with use of polyacrylic acid due to the presence of some acrylic acid of a low degree of polymerization especially where large areas of skin are contacted and where the user is subject to repeated contact with the cement.

The following examples are illustrative but not limiting of my invention.

EXAMPLE 1

345 grams anhydrous citrus acid and 260 grams ZnO were thoroughly mixed with 460 ml. isopropyl alcohol. While actively stirring this slurry, there was added as binder, a solution of 14 g. polyvinyl acetate (softening or heat-sealing temperature 230-240° F.) in 160 ml. methylene chloride. This slurry was spread on 32×28 mesh surgical gauze and passed through a drying oven at 230° F. to yield a dry, discontinuously coated gauze weighing about 210 g. per 4 inch by 5 yd. bandage roll. The coated gauze may weigh from 70 to 250 g. per roll. The gauze alone weighs about 18 g. The product was wet in water and the excess water squeezed out with very little loss of coating. The bandage warmed up almost immediately, became highly adhesive and very shortly took a hard set. The set material was still hard after standing in water for 4 days. The ZnO was very fine, 99.7% through 325 mesh screen and, of course, relatively insoluble in water. The citric acid was very soluble in water, 133 g. per 100 g. $H_2O$. The 375 g. citric used is equivalent to 209.7 g. ZnO, leaving 50 g. excess ZnO. I may use up to 300 % excess ZnO if I wish to reduce the temperature rise thereby, but preferably I use 10-25% in order to assure water resistance.

EXAMPLE 2

The experiment of Example 1 was repeated using 369 g. citric acid and 235 g. ZnO, and as binding agent 7 g. of the polyvinyl acetate dissolved in 160 ml. methyl cellosolve. The weight of coating was about ½ that of Example 1. When the product was wet in water and excess water squeezed out of the bandage roll, there was much less temperature rise and, although the final set was very hard, the set time was considerably longer than in Ex. 1. When soaked in water, the cast softened slightly. In this case the citric acid ZnO were chemically equivalent.

EXAMPLE 3

The experiment of Ex. 2 was repeated except that 454 g. citric acid and 151.2 g. ZnO were used. Results were similar to those of Ex. 2 but when soaked in water, the cast softened considerably. In this experiment there was excess citric acid.

EXAMPLE 4

Aged (and brittle) carboxylated cellulose, malonic acid, malic acid and maleic acid each was separately reacted with ZnO to produce adhesive material followed by formation of hard cement in a way similar to that with citric acid. One sample of tartaric acid, however, did not yield a "stringy" adhesive mass like with citric acid but it was found that this sample of tartaric acid was somewhat slow to wet in spite of being very soluble. In general it appears that polycarboxylic acids that are readily (quickly) soluble, considerably soluble and quickly wet show reaction with ZnO as does citric acid.

EXAMPLE 5

A portion of the ZnO of Ex. 1 was heated for several hours at 1000°-1100° C. and then mixed in the proportion of 375 g. dry, anhydrous citric acid and 260 g. of the ZnO. A small portion of this mixture was placed on one side of a glass plate and 6 drops (0.3 g.) water placed on another portion of the plate. Enough powder was mixed into the water with a spatula (as done in dental practice) to yield a thick paste whose set was delayed for about 8 minutes. This paste can be used as a so-called "surgical cement" by dentists as a temporary dental filling, a cavity liner, etc. or in orthopedics to assist in resetting of fractured bone material.

Control of the rate of reaction of ZnO is as above by heating or up to about 300% of the weight of the mix with finely-divided by dilution/MgO, $Bi_2O_3$, $Ca_3(PO_4)_2$ or Ca $F_2$ in the case of dentical or surgical use or, in the case of orthopedic bandages (Ex. 1), by use of coatings down to 70 g. per sq.ft., or by dilution with such finely divided solids as silica, clay, diatomaceous earth, etc., or by use of excess ZnO. The dilution is, of course, at some sacrifice of strength in the final cement. The set can also be slowed by using a larger proportion of water. While the particle size of the acid is not of great importance so long as it quickly wets and dissolves, it should be at least as fine as about 100 mesh. Increase of particle size of the ZnO, however, will effectively slow the set. A ½ hour heating at 800 to 900° C. is reported to decrease its rate of reaction with acid about 4-fold. This procedure is available from the manufacturer at a nominal cost. Some commercial ZnO is coated to the extent of about 0.5% by weight with propionic or lauric acid which forms the corresponding zinc salt by reaction on the surface of the ZnO, or the ZnO may be coated with other hydrophobic material like mineral oil which slows the wetting of the ZnO by water. The soluble acid should not have an ionization constant above about $10^{-3}$ for the first hydrogen in order not to be irritating on the skin for dental and surgical use and for such use, of course, should not be toxic or allergenic to most individuals.

ZnO is normally produced by air oxidation of pure Zn vapor (French process) or rotating of Zn ore with coal and subsequent oxidation (American process). In either case, the particle size is normally very small, 99–99.97% through 325 mesh and the % ZnO is 99.2–99.8. As indicated, however, some ZnO as received from the manufacturer has about 0.5% of the hydrophobic coating. ZnO may also be made by heating $ZnCO_3$ or I may use $ZnCO_3$ in place of ZnO in my adhesive cement. For surgical and dental use, U.S.P. XIII ZnO may be used although the commercial grade is very pure.

The examples show that cements using excess soluble acid over the chemical equivalent of the ZnO (Ex. 3), while yielding a highly adhesive product, are not water resistant as are those using equivalent amounts of ZnO and acid (Ex. 2) and the most highly water resistant are those using an excess of ZnO over acid (Ex. 1). In an orthopedic bandage, a water insoluble bonding agent can be used as in Examples 1-3. However in such a product, unless used to slow the wetting of the ZnO, the mix should not be completely covered with a binder that is neither water soluble nor water wettable. Water insoluble but water wettable binders are (1) dextran which can be used in solution in anhydrous methanol, ethanol, propanol or isopropanol as a slurry product (2) Zein dissolved in a mixture of methylene chloride and methanol. Bonding agents that can be used to slow the wetting are (1) solutions of polyvinyl acetate in toluene, methyl cellosolve or methylene chloride (2) ethyl cellulose and other water insoluble, inert materials in anhydrous solution (3) copolymers of vinyl acetate and acrylate or methacrylate esters in solvents such as toluene or methylene chloride (4) solutions of shellac, silicones or cellulose acetate in anhydrous solvents. However, such binders must be applied so as not to form continuous coatings i.e. they must be applied as finely divided dispersions of the solid materials so as to leave at least some areas uncovered.

In the ways described the set may be slowed as desired. Slowing the set also limits the temperature rise. When covering a considerable area of the human body with the bandage described, one does not want the temperature to exceed about 140° F. This is achieved by slowing the set as described, using excess water, diluting with inert materials as described, using excess reactants or by combinations of these devices.

In order to further strengthen and waterproof my cement, I may add an uncured melamine-formaldehyde resin with a mol ratio of melamine to formaldehyde from about 1:1.5 to 1:3.3 and preferably from 1:1.7 to 1:2.5, respectively; in amount from 5 to 30% by weight based on solids in the adhesive, preferably 10 to 20%. An acid reacting resin condensation catalyst is also included in amount from 1 to 10% of the weight of resin and comprising one or more of the following: ammonium chloride, a mixture of equivalent amounts of ammonium sulfate and potassium chloride, stannous chloride dihydrate and aluminum chloride hexahydrate. Any of the anhydrous slurry liquids disclosed may be used, following the procedures of U.S. Pat. No. 2,842,120. When using such resin, I also prefer to use polyvinyl pyrrolidone of molecular-weight 10,000 to 360,000 in amount from 10 to 150% of the weight of resin, as in U.S. Pat. No. 3,671,280, with a preference for 50 to 100%. The resin condensation catalyst may be omitted from the slurry and applied in solution or suspension, for example, with or without water soluble polyethylene glycol of melting-point slightly above room temperature, in anhydrous methanol or methanol and methylene chloride, to the dried bandage when the adhesive cement is used to produce bandage.

It should be added that, in the case of the orthopedic bandage, the use of a bonding agent to bend the particles of the spread to themselves and to the backing, such an agent is not necessarily used but when used is in amount from 0.5 to 1.5 percent of the weight of the spread.

The properties hereinbefore cited as required of those polycarboxylic acids I find useful, will distinguish them from among the possible polycarboxylic acids-- which are extremely numerous, for example, when one considers the various halogen substitution products of even the more than 20 simple dibasic acids let alone the polyhalogen and mixed halogen plus the alkyl and aryl group substitution products of the higher polycarboxylic acids and the numerous permutations of and with the various possible substituents.

While in so called "surgical cements", up to about 10 percent of the weight of the zinc oxide may be replaced by MgO, $Bi_2O_3$, $Ca_3(PO_4)_2$ or $CaF_2$, I prefer to use ZnO alone.

While I have mentioned using up to about 300% of the equivalent amounts of acid or oxide, I may upon occasion use as much as 400% excess, but not less than 10% of the equivalent of either oxide or acid. If I wish to keep the acid separate from the dry oxide before use, I may provide the acid in aqueous solution at any desired concentration from its saturation value to give the strongest cement and the fastest reaction, down to about 10% by weight to slow the reaction at the expense of some sacrifice of strength. The use of dilute acid will, of course, also reduce the reaction temperature.

The polyacrylic acids of the prior art are (1) not only polybasic but are also polymeric whereas many of the acids I use are monomeric (2) the polyacrylic acids are unsaturated, i.e. they contain double bonds which are conducive to polymerization and formation of viscous solutions while many of my acids are saturated and do not form highly viscous solutions even in high concentrations. When the prior art polyacrylic acid solutions are evaporated in an attempt to obtain solid acid, they form glassy non-porous, non-absorptive solids and not the quickly wettable and thoroughly wettable acids I require and, in such form, are not suitable for forming my adhesives and cements. However, I have been able to obtain powdery, finely-divided, quickly and thoroughly wettable solid polyacrylic acids by (1) freeze-drying their aqueous solutions, i.e. drying the frozen solutions under high vacuum without melting and (2) drying of aqueous solutions at low temperature by keeping them diluted with water-soluble, volatile solvents such as acetone, methyl and ethyl alcohol until all water is removed. I am thus able to use solid polyacrylic acids of molecular-weight between 15000 and 150000 as I do citric acid; and similarly polymethacrylic acid.

It should be mentioned that acids such as the tartaric hereinbefore mentioned, when mixed with zinc oxide and wet, form small clumps but not highly adhesive, stringy mass as does citric acid. While usually many of my dry acids and oxides do not separately appear to be sensitive to moisture, I have discovered that the stored mixture of zinc oxide, for example, and citric acid must be thoroughly protected from even the moisture in the air, preferably by metal foil or ethylidene chloride (Saran). Ordinary 5-mil. polyethylene film is inadequate.

In the case where my cement is strengthened by addition of melamineformaldehyde resin, as distinguished from its use to waterproof an orthopedic cast, I may use a mix of cement and resin containing from 10 to as much as 90% by weight of resin and, with use of the resin, it is again necessary to thoroughly dry and thoroughly protect from moisture in storage. When thoroughly dry, all ingredients as disclosed, including catalyst, may be combined: or condensation catalyst, polycarboxylic acid and polyvinyl pyrrolidone either in solid form or in aqueous solution, may be combined and kept separate in storage from dry resin mixed with dry zinc oxide. When no contact with the human body is involved in use, the polyvinyl pyrrolidone (which preferably has an average molecular-weight of about 40000) may be omitted.

Having thus described my invention, what I claim is:

1. An intimate mixture of finely-divided, dry zinc oxide and a dry, solid, weak, powdered, unpolymerized polycarboxylic acid which acid is such as to rapidly wet and largely dissolve in water, said mixture being maintained dry and unreacted until use; its dry particles being bonded together by a dry, water-insoluble agent in the amount of the order of about 1–2% by anhydrous weight of the mix which bonding agent does not materially interfere with rapid wetting of said mixture when contacted with water and, when wetted, rapidly becomes adhesive and quickly sets to a strong, hard cement; the proportions of said oxide and said acid in said mixture being from 10 to 400 percent of their chemical equivalence, said cement being relatively resistant to distintegration in water when the proportion of said oxide is such as to be at least chemically equivalent to the acid in said mixture.

2. The product of claim 1 wherein the said zinc oxide has been inactivated by heating.

3. A dry mixture of the said zinc oxide and the said acid of claim 8, protected from absorption of moisture, 4. The product of claim 1 wherein the said zinc oxide has been inactivated by a thin hydrophobic coating.

5. The product of claim 1 wherein the said acid is citric acid.

6. The product of claim 5 wherein the said acid is citric acid and the said zinc oxide is in amount from 10 to 25 percent in excess of its chemical equivalent of said citric acid.

7. The product of claim 1 wherein the said zinc oxide is replaced by zinc carbonate.

8. The product of claim 1 wherein the said zinc oxide has been coated with about 0.5 percent of its weight of a hydrophobic zinc salt that slows its wetting with water.

9. The product of claim 1 wherein about 10 percent of the weight of the said zinc oxide has been replaced with at least one finely-divided, dry, inert material selected from the class consisting of $MgO$, $Bi_2O_3$, $Ca_3(PO_4)_2$, $CaF_2$, silica, clay and diatomaceous earth.

10. The product of claim 1 wherein the said acid is selected from at least one of the acids in the class consisting of citric acid, carboxylated cellulose, malonic acid, malic acid, and maleic acid.

* * * * *